US007088250B2

(12) United States Patent
Yasushi

(10) Patent No.: US 7,088,250 B2
(45) Date of Patent: Aug. 8, 2006

(54) APPARATUS AND METHOD FOR ESTIMATING FATIGUE LEVEL

(75) Inventor: Mitsuo Yasushi, Tsurugashima (JP)

(73) Assignee: Pioneer Corporation, Tokyo-to (JP)

( * ) Notice: Subject to any disclaimer, the term of this patent is extended or adjusted under 35 U.S.C. 154(b) by 197 days.

(21) Appl. No.: 10/648,345

(22) Filed: Aug. 27, 2003

(65) Prior Publication Data

US 2004/0046666 A1 Mar. 11, 2004

(30) Foreign Application Priority Data

Aug. 29, 2002 (JP) .......................... P2002-250076

(51) Int. Cl.

| | |
|---|---|
| ***G08B 23/00*** | (2006.01) |
| ***G08B 13/00*** | (2006.01) |
| ***A61B 5/02*** | (2006.01) |
| ***A61B 5/00*** | (2006.01) |
| ***A61B 5/08*** | (2006.01) |

(52) U.S. Cl. .................. 340/573.1; 340/574; 340/575; 340/576; 600/300; 600/301; 600/484

(58) Field of Classification Search ............ 340/573.1, 340/574–576, 425.5, 465; 180/271–272; 600/300–301, 484; 128/639, 666, 687, 702, 128/706–709

See application file for complete search history.

(56) References Cited

U.S. PATENT DOCUMENTS

| | | | | |
|---|---|---|---|---|
| 4,664,127 | A | 5/1987 | Ikeyama | 128/689 |
| 4,706,072 | A * | 11/1987 | Ikeyama | 340/576 |
| 5,769,085 | A * | 6/1998 | Kawakami et al. | 600/519 |
| 5,783,997 | A * | 7/1998 | Saitoh et al. | 340/576 |
| 5,813,989 | A * | 9/1998 | Saitoh et al. | 600/484 |
| 6,104,296 | A * | 8/2000 | Yasushi et al. | 340/576 |

FOREIGN PATENT DOCUMENTS

| | | |
|---|---|---|
| EP | 0 712 604 | 5/1996 |
| JP | 2002065650 | 3/2002 |

* cited by examiner

*Primary Examiner*—Daniel Wu
*Assistant Examiner*—Lam Pham
(74) *Attorney, Agent, or Firm*—Drinker Biddle & Reath LLP

(57) ABSTRACT

A fatigue-level estimation apparatus is provided. The apparatus comprises a heat rate calculator and a fatigue level estimator. The heart rate calculator receives a signal indicative of a heartbeat of an object to be estimated to calculate a heart rate signal changing sequentially in time. The fatigue level estimator estimates a fatigue level of the object by detecting a sharp and transient rise in the heartbeat in the heart rate signal. The fatigue-level estimation has less influence resulting from individual differences, while still maintaining high reliability in the estimation.

17 Claims, 14 Drawing Sheets

18 MEMORY
14 15a 16a 17 13
11 ELECTROCARDIOGRAM MEASURING DEVICE
12 HEART-RATE MEASURING DEVICE
AVERAGE MEASURING SECTION
THRESHOLD SETTING SECTION
ELAPSED-TIME MEASURING SECTION
THRESHOLD SETTING SECTION
ELAPSED-TIME MEASURING SECTION
COMPARISON /OUTPUT SECTION
15b 16b
ALARM DEVICE 19
FATIGUE-LEVEL DISPLAYING DEVICE 20

13
COMPARISON /OUTPUT SECTION
17
ELAPSED-TIME MEASURING SECTION
16a
ELAPSED-TIME MEASURING SECTION
16b
MEMORY
18
THRESHOLD SETTING SECTION
15a
THRESHOLD SETTING SECTION
15b
AVERAGE MEASURING SECTION
14
FATIGUE-LEVEL DISPLAYING DEVICE
20
ALARM DEVICE
19
HEART-RATE MEASURING DEVICE
12
ELECTROCARDIOGRAM MEASURING DEVICE
11

33
COMPARISON/OUTPUT SECTION
17
MEMORY
18
LOCAL-MAXIMAL-VALUE MEASURING SECTION
34a
LOCAL-MINIMAL-VALUE MEASURING SECTION
34b
FATIGUE-LEVEL DISPLAYING DEVICE
20
ALARM DEVICE
19
AVERAGE MEASURING SECTION
14
PEAK DETECTING/CALCULATING SECTION
32
ELECTROCARDIOGRAM MEASURING DEVICE
11

APPARATUS AND METHOD FOR ESTIMATING FATIGUE LEVEL

BACKGROUND OF THE INVENTION

The present invention relates to a method and apparatus for estimating a fatigue level of an object to be estimated, and a program applicable to such method and apparatus.

Conventionally, this type of fatigue-level estimation apparatus has been disclosed by, for example, Japanese Patent Laid-open (KOKAI) No. 2002-65650. In this fatigue-level estimation apparatus, a heart rate and variations in heartbeat intervals in both of a non-driving state and a driving state are computed on the basis of a driver's heart rate signal. Both of the heart rate and the changes in the heartbeat intervals are developed onto a two-dimensional coordinate so as to form a map thereon so that a temporal transition trend of the map is observed. By considering this temporal transition trend, in addition to consideration about whether or not there is an instantaneous rise in the heart rate, a driver's fatigue level is estimated.

In the estimation process according to this conventional fatigue-level estimation apparatus, it is estimated that the mutually closer both of the maps in between the non-driving and driving states on the two-dimensional coordinate (of which two dimensions are the heart rate and the changes in the heartbeat intervals are), the higher the driver's fatigue level is.

However, the conventional fatigue-level estimation apparatus is configured such that the fatigue level is obtained through the comparison with past data. Thus, if the past data is unreliable, the reliability of resultant estimation of the fatigue level is forced to decrease. Since there are great differences among individuals in estimating the fatigue level, the estimation should be done every driver.

In addition, the conventional fatigue-level estimation apparatus has no configuration to take it consideration the factors, such as drivers' personal differences, drivers' physical conditions, and vehicle running conditions on roads. Thus, it is difficult for the conventional apparatus to determine whether a driver is really tired or not. Further, in order to avoid erroneous detection of the fatigue level, detection sensitivity can be lowered. But, if such a measure is taken, there is a possibility that failure in the detection is caused.

SUMMARY OF THE INVENTION

The present invention has been made in view of the above circumstances, and an object of the present invention is therefore to provide an apparatus, method, and computer-readable program, which are directed to estimation of a fatigue level of an object which can be carried out in such a manner that there are less individual differences in the estimation, there is resistance to erroneous estimating operations, and the fatigue level can be estimated with higher reliability using only heartbeat information.

In order to realize the above object, as one aspect, the present invention provides a fatigue-level estimation apparatus comprising: a heart rate calculator configured to receive a signal indicative of a heartbeat of an object to be estimated to calculate a heart rate signal changing sequentially in time; and a fatigue level estimator configured to estimate a fatigue level of the object by detecting a sharp and transient rise in the heartbeat in the heart rate signal calculated by the heart rate calculator.

It is preferred that the fatigue level estimator comprises an average heart-rate calculating unit configured to calculate an average heart rate over a specified period of time on the basis of the heart rate signal; a first elapsed-time measuring unit configured to measure an elapsed time during which the heart rate signal is over the average heart rate; a second elapsed-time measuring unit configured to measure an elapsed time during which the heart rate signal is below the average heart rate; and a comparison output unit configured to draw a comparison between the elapsed times measured by the first and second elapsed-time measuring units to output information indicative of the fatigue level.

It is also preferred that the fatigue level estimator comprises an average heart-rate calculating unit configured to calculate an average heart rate over a specified period of time on the basis of the heart rate signal; a first variance-value calculating unit configured to calculate a variance-value in a temporal range during which the heart rate signal is over the average heart rate; a second variance-value calculating unit configured to calculate a variance-value in a temporal range during which the heart rate signal is below the average heart rate; and a comparison output unit configured to draw a comparison between the variance-values calculated by the first and second variance-value calculating units to output information indicative of the fatigue level.

As another aspect of the present invention, there is provided a fatigue-level estimation apparatus comprising: a peak-to-peak interval calculator configured to detect a peak value in a predetermined measurement range of a signal indicative of a heartbeat of an object to be estimated and to calculate a peak-to-peak interval from the peak value; and a fatigue level estimator configured to measure an average value of the peak-to-peak interval calculated by the peak-to-peak interval calculator and to draw a comparison between an amplitude over the average value and a further amplitude over the average value for estimating a fatigue level of the object.

In the foregoing configurations, it is preferred that the apparatus further comprises an alarm unit configured to issue an alarm when the fatigue level of the object estimated by the fatigue level estimator becomes larger than a predetermined value.

Still, preferably, the apparatus further comprises a display unit configured to display pieces of information in relation to the fatigue level of the object estimated by the fatigue level estimator.

Still, as another aspect of the present invention, there is provided a fatigue-level estimation method comprising the steps of: receiving a signal indicative of a heartbeat of an object to be estimated to calculate a heart rate signal changing sequentially in time; and estimating a fatigue level of the object by detecting a sharp and transient rise in the heartbeat in the calculated heart rate signal.

Still, as another aspect of the present invention, there is provided a computer-readable program for estimating a fatigue level, the program being executed by a computer provided in a fatigue-level estimation apparatus, the computer achieving the functions of: heart rate calculating means for receiving a signal indicative of a heartbeat of an object to be estimated to calculate a heart rate signal changing sequentially in time; and fatigue level estimating means for estimating a fatigue level of the object by detecting a sharp and transient rise in the heartbeat in the heart rate signal calculated by the heart rate calculating means.

BRIEF DESCRIPTION OF THE DRAWINGS

Other objects and aspects of the present invention will become apparent from the following description and embodiments with reference to the accompanying drawings in which.

DETAILED DESCRIPTION OF THE PREFERRED EMBODIMENTS

Preferred embodiments of an apparatus, method, and computer-readable program for estimating a fatigue level of an object to be estimated will now be described with reference to accompanying drawings.

First Embodiment

Referring to FIGS. 1 to 6, a first embodiment of the fatigue-level estimation apparatus will now be described, in which the estimation method and computer-readable program will be explained together in terms of their functions.

Figure 1:
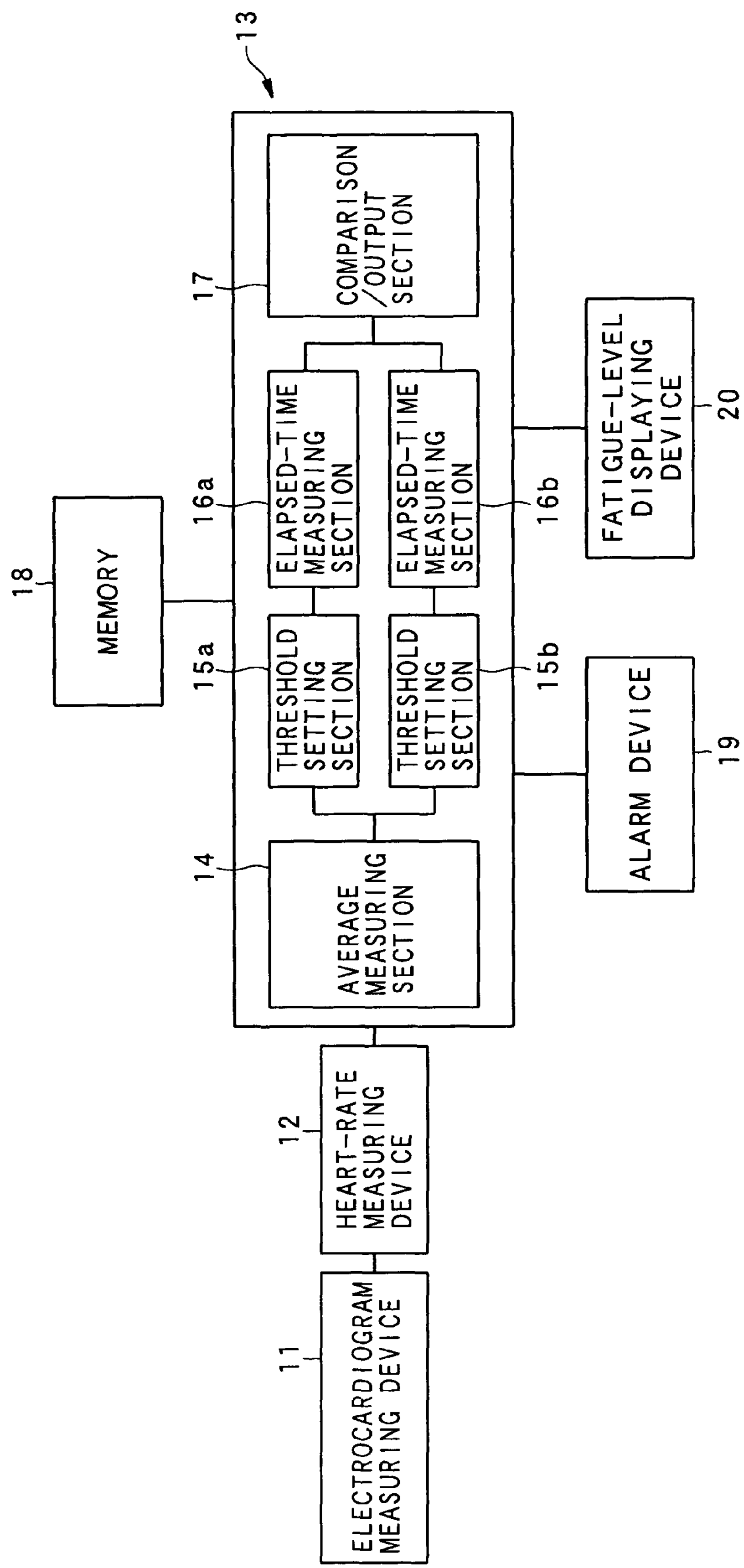
FIG. 1 is a block diagram showing the configuration of a fatigue-level estimation apparatus according to a first embodiment of the present invention.

FIG. 1 is a block diagram showing the configuration of the fatigue-level estimation apparatus according to the first embodiment. This apparatus, which is mounted on moving objects such as vehicles, is configured to receive a signal indicative of heart rates of a driver who is an object to be estimated, detect a heart rate based on the heart rate signal, and estimate a driver's fatigue level using the heart rate signal. In this embodiment, the signal indicative of the driver's heartbeat is produced from an electrocardiogram measuring device of which sensor is embedded in a steering wheel. This sensing system is also true of other embodiments will be described later.

As shown in FIG. 1, the fatigue-level estimation apparatus according to the present embodiment comprises an electrocardiogram measuring device 11 detecting electrocardiogram information of an object to be estimated; a heart-rate measuring device 12 receiving a heartbeat signal indicative of object's heartbeats from the electrocardiogram information to calculate a heart rate signal changing sequentially in time; and an analysis unit 13 estimating a fatigue level of the object by detecting a sharp and transient rise in the heartbeat in the heart rate signal calculated by the heart-rate measuring device 12. The fatigue-level estimation apparatus further comprises a memory 18 that is in charge of transmitting and receiving data to and from the analysis unit 13 and making the analysis unit 13 work in compliance with a predetermined program for estimation of the fatigue level; an alarm device 19, which is composed of for example, a buzzer, that issues an alarm in cases where the object's fatigue level estimated by the analysis unit 13 exceeds a predetermined value; and a fatigue-level displaying device 20 displaying in real time information about the fatigue level estimated by the analysis unit 13.

In these components, the heart-rate measuring device 12 composes the heart-rate calculating unit according to the present embodiment, the analysis unit 13 composes the fatigue-level estimating unit according to the present invention, the alarm device 19 corresponds to the an alarm unit according to the present invention, and the fatigue-level displaying device 20 corresponds to the display unit according to the present invention.

The electrocardiogram measuring device 11 has, as described above, a sensor part (not shown) to detect a driver's heartbeat signal at part of the steering wheel. Driver's grasp of the sensor part with both hands makes it possible to obtain a heartbeat signal, that is, temporal changes in action potential of the driver's heart. The electrocardiogram measuring device 11 produces electrocardiogram waveform data based on temporal changes in the action potential and outputs a heartbeat signal based on such waveform data.

In measuring a heart rate, the heart-rate measuring device 12 calculates a value indicative of intervals between R-waves each showing a maximum during each cardiac cycle of the electrocardiogram waveform data produced by the electrocardiogram measuring device 11 (that is, peak-to-peak interval data). The device 12 then obtains a heart rate per minute by computing a reciprocal of the peak-to-peak interval data and then multiplying the reciprocal by 60. A signal indicating the calculated heart rate is sent to the analysis unit 13.

The analysis unit 13 is responsible for estimating a fatigue rate by catching a variation in the heartbeat, which shows a sharp and transient rise in the heartbeat, in the heartbeat rate signal calculated by the heart-rate measuring device 12.

Practically, the analysis unit 13 according to the present embodiment comprises an average measuring section 14 configured to calculate an average heart rate over a specified period of time on the basis of the heart rate signal; a threshold setting section 15*a* configured to set a threshold higher than the average heart rate by a specified offset amount; a second threshold setting section 15*b* configured to set a second threshold lower than the average heart rate by a specified offset amount; a first elapsed-time measuring section 16*a* configured to measure an elapsed time during which the heart rate signal is over the average heart rate; a second elapsed-time measuring section 16*b* configured to measure an elapsed time during which the heart rate signal is below the average heart rate; and a comparison/output section 17 configured to draw a comparison between the elapsed times measured by the first and second elapsed-time measuring sections 16*a* and 16*b* to output information indicative of a fatigue level.

In the present embodiment, the average measuring section 14 corresponds to the average heart-rate calculating unit of the present invention, both the threshold setting section 15*a* and the elapsed-time measuring section 16*a* compose the first elapsed-time measuring unit of the present invention, both the threshold setting section 15*b* and the elapsed-time measuring section 16*b* compose the second elapsed-time measuring unit of the present invention, and the comparison/output section 17 corresponds to the comparison output unit of the present invention, respectively.

Figure 2:
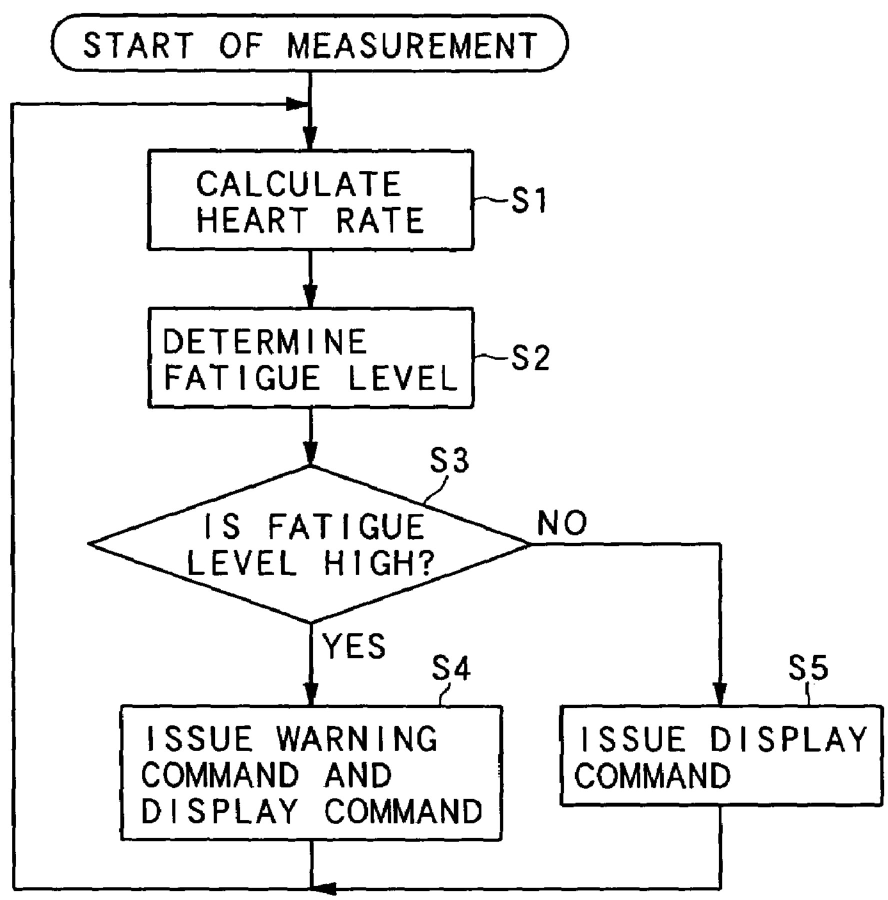
FIG. 2 is a flowchart showing the procedures for fatigue-level estimation processing carried out in the first embodiment.

Referring to FIG. 2, the processing for estimating a fatigue level carried out in this embodiment will now be described.

A heartbeat signal indicative of the heartbeats of an object to be estimated, which is produced from object's electrocardiogram information measured by the electrocardiogram measuring device 11, is inputted to the heart-rate measuring device 12, at which a heart rate signal changing sequentially in time is calculated (step S1). Practically, the heart-rate measuring device 12 calculates the heart rate every 10 seconds and sends out the signal indicating the heart rate.

Then, the analysis unit 13 carries out fatigue-level estimation processing with the use of the heart rate signal (step S2). This processing will be detailed with reference to FIG. 3.

The analysis unit 13 further determines whether or not a driver's fatigue level is large (step S3). If the fatigue level is over a predetermined level, the analysis unit 13 sends out an alarm command signal to the alarm device 19 and a display command signal to the fatigue-level displaying device 20 (step S4). Thus, the alarm device 19 issues an alarm, while the fatigue-level displaying device 20 provides a screen showing the fatigue level.

In contrast, when the fatigue level is below the predetermined level at step S3, the analysis unit 13 drives the fatigue-level displaying device 20 by a display command signal, so that the device 20 displays a fatigue condition in real time (step S5).

Figure 3:
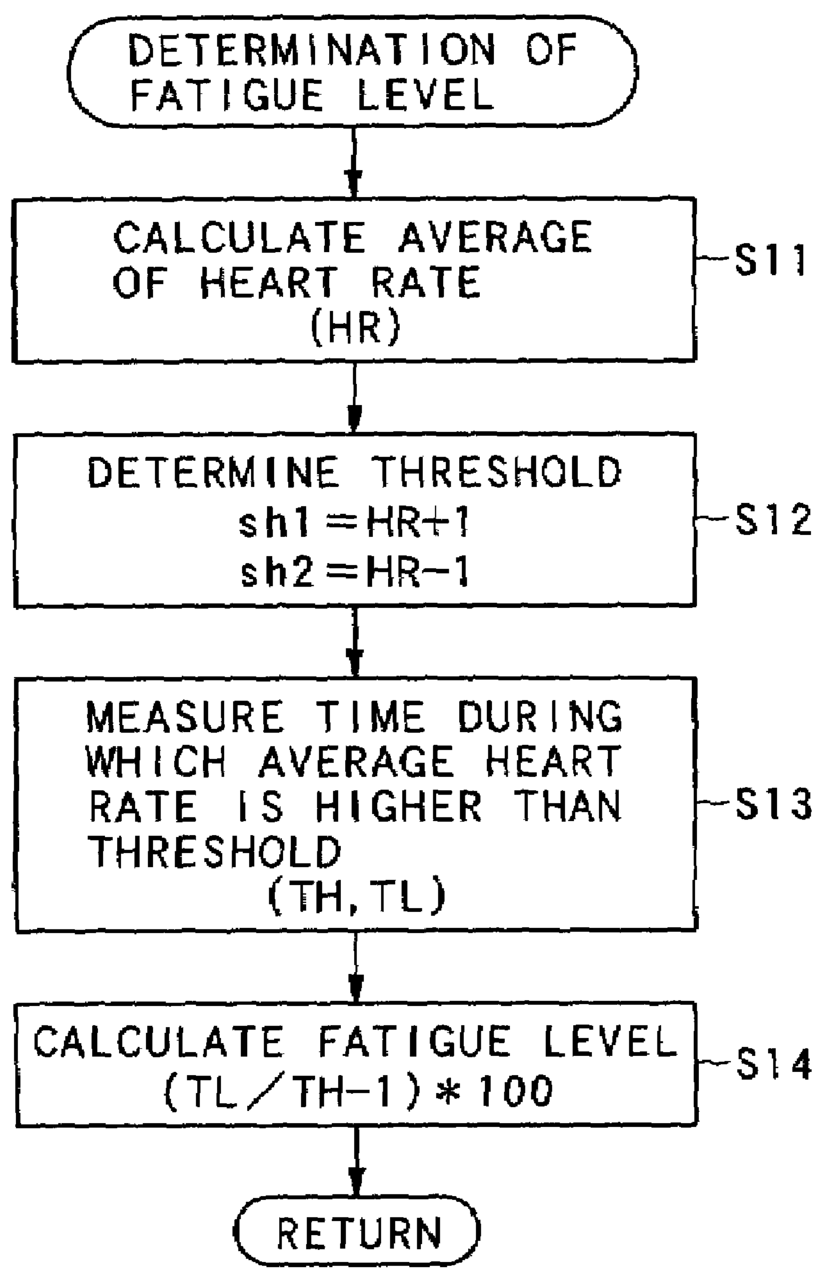
FIG. 3 is a flowchart detailing how to estimate a fatigue level, which is included in the procedures shown in FIG. 2.

Referring to a flowchart shown in FIG. 3, the fatigue-level estimation processing at step S2 will now be detailed.

First, the heart-rate measuring device 12 figures out a heart rate every 10 seconds, which is fed to the average measuring section 14 of the analysis unit 13. Hence the average measuring section 14 calculates an average heart rate over a specified measurement period of 100 seconds (i.e., approximately 17 minutes). This average heart rate is denoted as HR (step S11).

The analysis unit 13 then specifies thresholds toward the average heart rate HR. To be specific, by the threshold setting section 15*a*, a specific amount (in this case, an amount of one heart rate) is offset from the average heart rate to specify an upper threshold sh1 higher than the average heart rate HR. In parallel, by the remaining threshold setting section 15*b*, a lower threshold sh2 lower than the average heart rate HR is specified. Accordingly, the upper threshold sh1 is set to an amour of the "average heart rate+1," whilst the lower threshold sh2 is set to an amount of the "average heart rate−1." (step S12).

Figure 4:
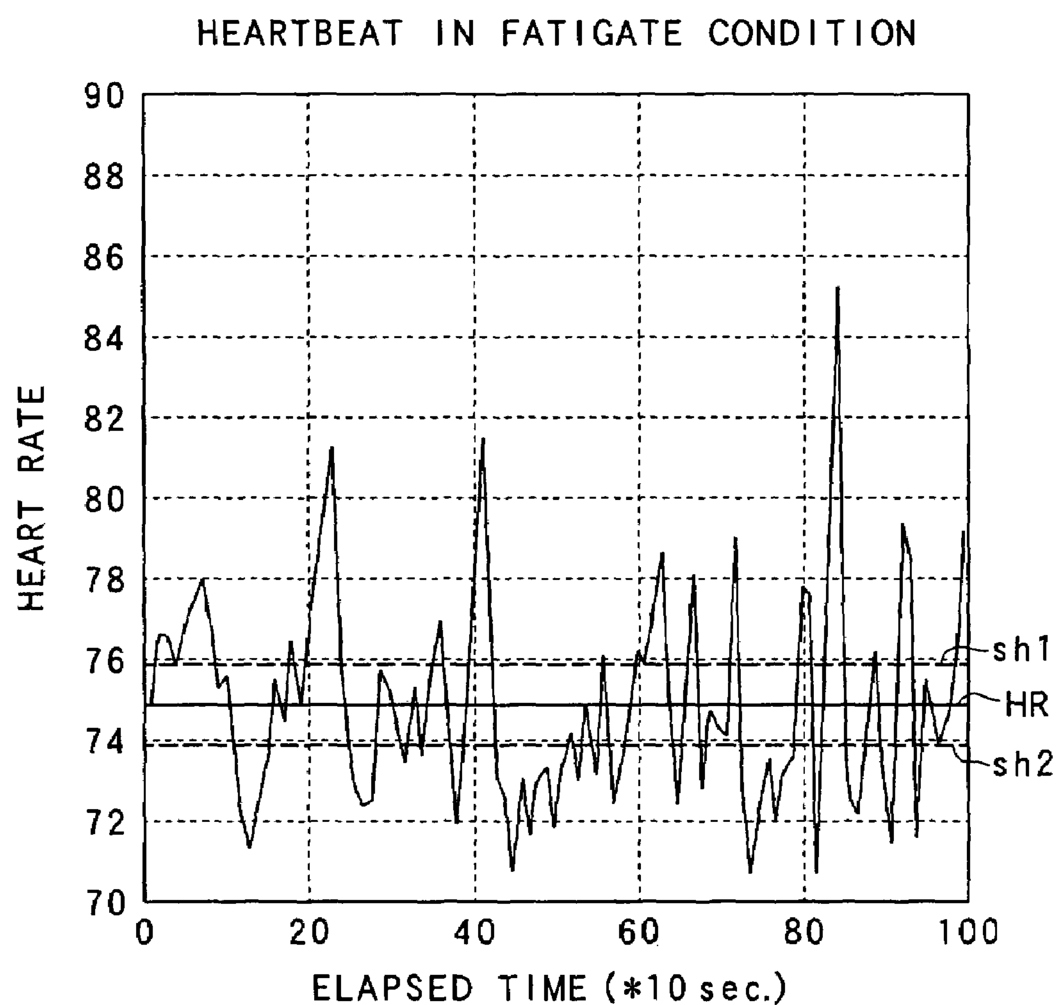
FIG. 4 is a graph indicating temporal changes in a driver's heart rate, the driver being in travel along a highway and feels tired.
Figure 5:
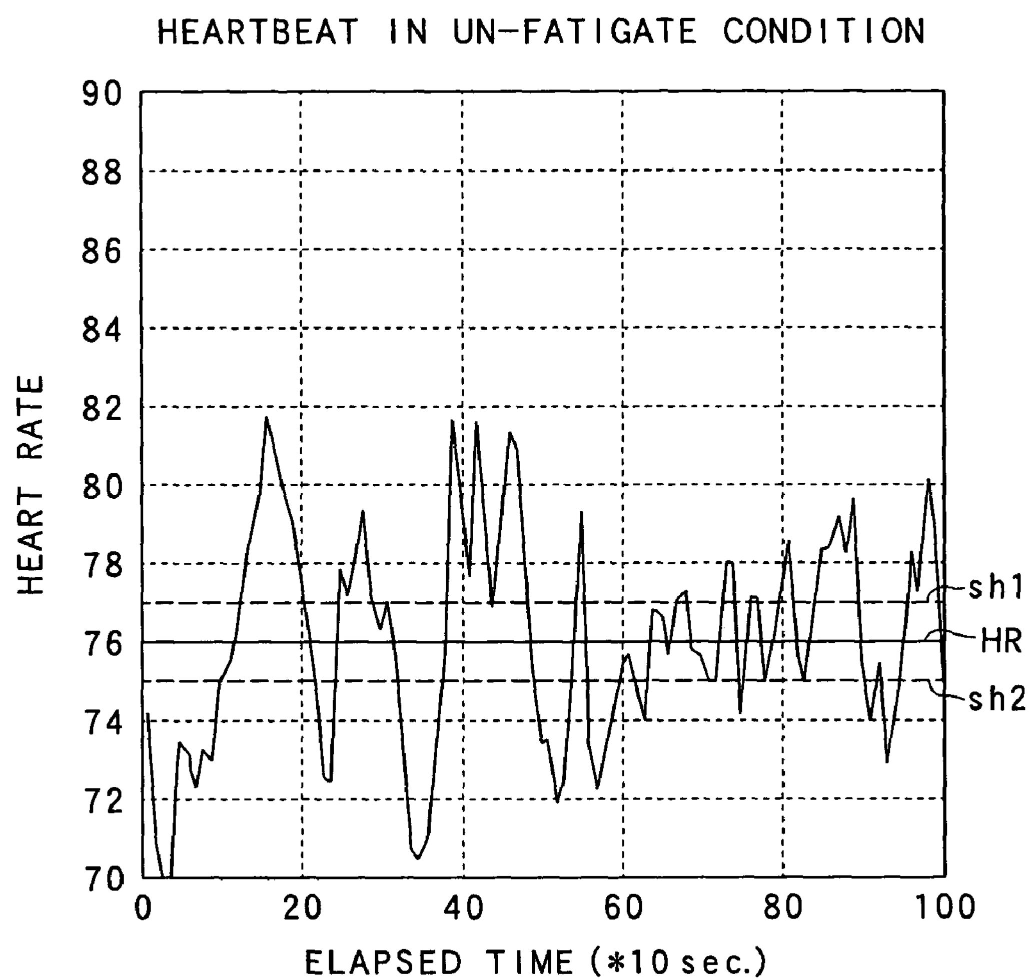
FIG. 5 is a graph indicating temporal changes in a driver's heart rate, the driver being in travel along an urban road and does not feel tired.

By way of example, as shown in FIGS. 4 and 5, the average heart rate is 75, while the upper threshold sh1 is 76 and the lower threshold is 74.

Further, a range of elapsed time during which the heart rate is over the upper threshold sh1, which is denoted as TH, is calculated by the elapsed-time measuring section 16*a*. At the dame time, a range of elapsed time during which the heart rate is below the lower threshold sh2, which is denoted as TL, is calculated by the remaining elapsed-time measuring section 16*b* (step S13).

The comparison/output section 17 draws a comparison between one elapsed time TH, during which the heart rate is over the average, and the other elapsed time TL, during which the heart rate is below the average, and provides information showing a fatigue level based on compared results (step S14).

That is, the above comparison is carried out on the following formula for defining a driver's fatigue level F.

$$F=(TL/TH-1)\times 100$$

FIG. 4 is a graph resulting from an actual test and indicates temporal changes in a driver's heart rate, the driver being in travel along a highway and feels tired. As shown in FIG. 4, the number of heart rate data to be measured was 100 points, while it was found that heart rates over the upper threshold sh1 ranged over 30 points and heart rates below the lower threshold sh2 ranged over 41 points. As a result, the fatigue level F is:

$$F=(41/30-1)\times 100=41.$$

In this case, when the heart rate is over a predetermined threshold 30, estimation is made such that the driver is tired. But, in cases where the heart rate is blow the threshold 30, it is estimated that the driver is yet to be tired.

In the above condition, the fatigue level F=41 is over the threshold 30, so that the estimation that the driver has been tired is made. This fatigue condition is displayed on the fatigue-level displaying device 20 in such a mode shown in FIG. 6, for instance, while an alarm is outputted from the alarm device 19.

On the other hand, FIG. 5 is a graph on an actual test and indicates temporal changes in a driver's heart rate, the driver being in travel along an urban road and does not feel tired. As shown in FIG. 5, the number of heart rate data to be measured was 100 points, while it was found that heart rates over the upper threshold sh1 ranged over 39 points and heart rates below the lower threshold sh2 ranged over 39 points. As a result, the fatigue level F is:

$$F=(39/39-1)\times 100=0.$$

Accordingly, since the fatigue level F is zero, which is smaller than the predetermined threshed 30, resulting in that it can be estimated such that the direr has yet to be tired. In this case, the value of the fatigue level F is displayed in real time on the fatigue-level displaying device 20, as exemplified in FIG. 6.

Figure 6:
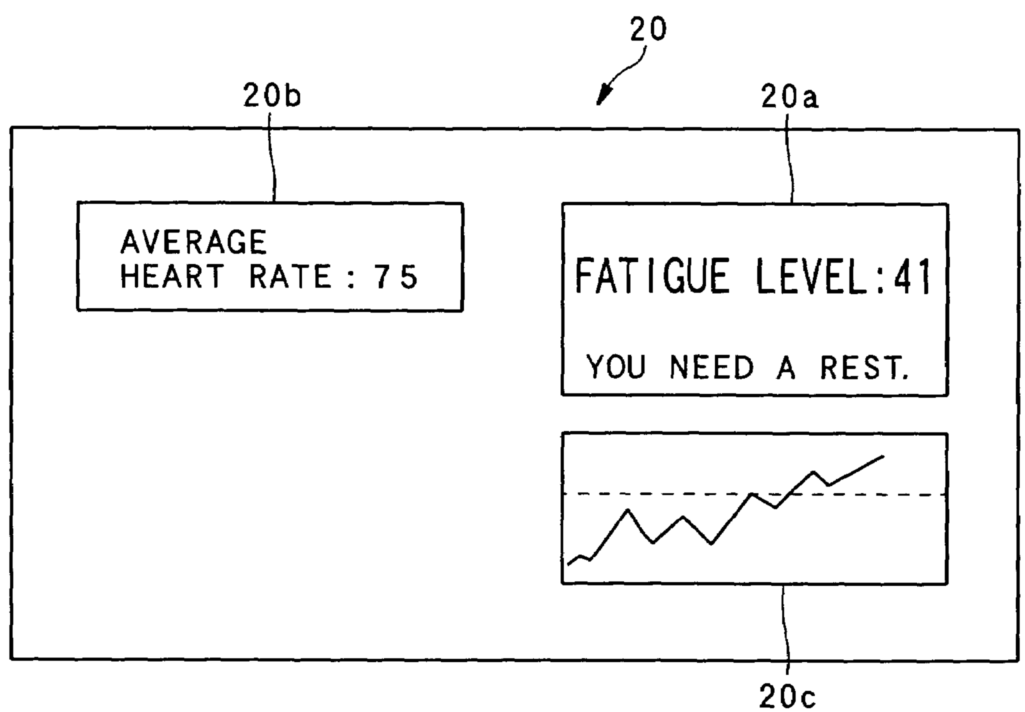
FIG. 6 is an enlarged view illustrating the screen of a fatigue-level display device.

The fatigue-level displaying device 20 has a screen shown in FIG. 6, where there is a fatigue-level display area 20*a*. This area 20*a* provides a numeral value showing the measured fatigue level F as well as a massage, if the fatigue level F is high, saying that "You need a rest," so that the driver is urged to take a rest. On the screen of the device 20, there are also formed a heart-rate display area 20*b* and a waveform display area 20*c*, data a, the forearm of which displays the average heart rate and the latter of which provides a representative waveform of the heart rates thereon.

As described above, the fatigue-level estimation apparatus according to the present embodiment is provided with a heart-rate measuring device 12 receiving a heartbeat signal indicative of object's heartbeats from the electrocardiogram information to calculate a heart rate signal changing sequentially in time and the analysis unit 13 estimating a fatigue level of the object by detecting a sharp and transient rise in the heartbeat in the heart rate signal. Hence, with less personal differences in the heart rate estimation and with resistance to erroneous operations in the heart rate estimation, the fatigue level can be estimated at higher reliability by using only heartbeat information, without making use of variety of types of information about running conditions of a vehicle.

Furthermore, in the present embodiment, the analysis unit 13 is provided with the average measuring section 14 configured to calculate an average heart rate over a specified period of time on the basis of the heart rate signal, the elapsed-time measuring section 16*a* configured to measure an elapsed time during which the heart rate signal is over an average heart rate, the elapsed-time measuring section 16*b* configured to measure an elapsed time during which the heart rate signal is below the average heart rate, and the comparison/output section 17 configured to draw a comparison between the elapsed times measured by the elapsed-time measuring sections 16*a* and 16*b* to output information indicative of a fatigue level. Therefore, without using various types of information in relation to running conditions of a vehicle, the heartbeat information can be used alone to figure out higher-reliability fatigue levels. In the estimation process, the personal differences can be reduced and the erroneous operations can be lessened.

Furthermore, in the present embodiment, there is also the alarm device 19 configured to output an alarm when a driver's fatigue level estimated by the analysis unit 13 becomes larger than a predetermined value. The driver can easily understand that he or she is tired and needs a rest.

Still further, in the present embodiment, the fatigue-level displaying device 20 is placed to display in real time pieces of information in relation to the fatigue level estimated by the analysis unit 13. This provides constantly a driver with information about at which fatigue level the driver drives a vehicle.

Second Embodiment

Referring to FIGS. 7 to 10, a second embodiment of the present invention will now be described.

Figure 7:
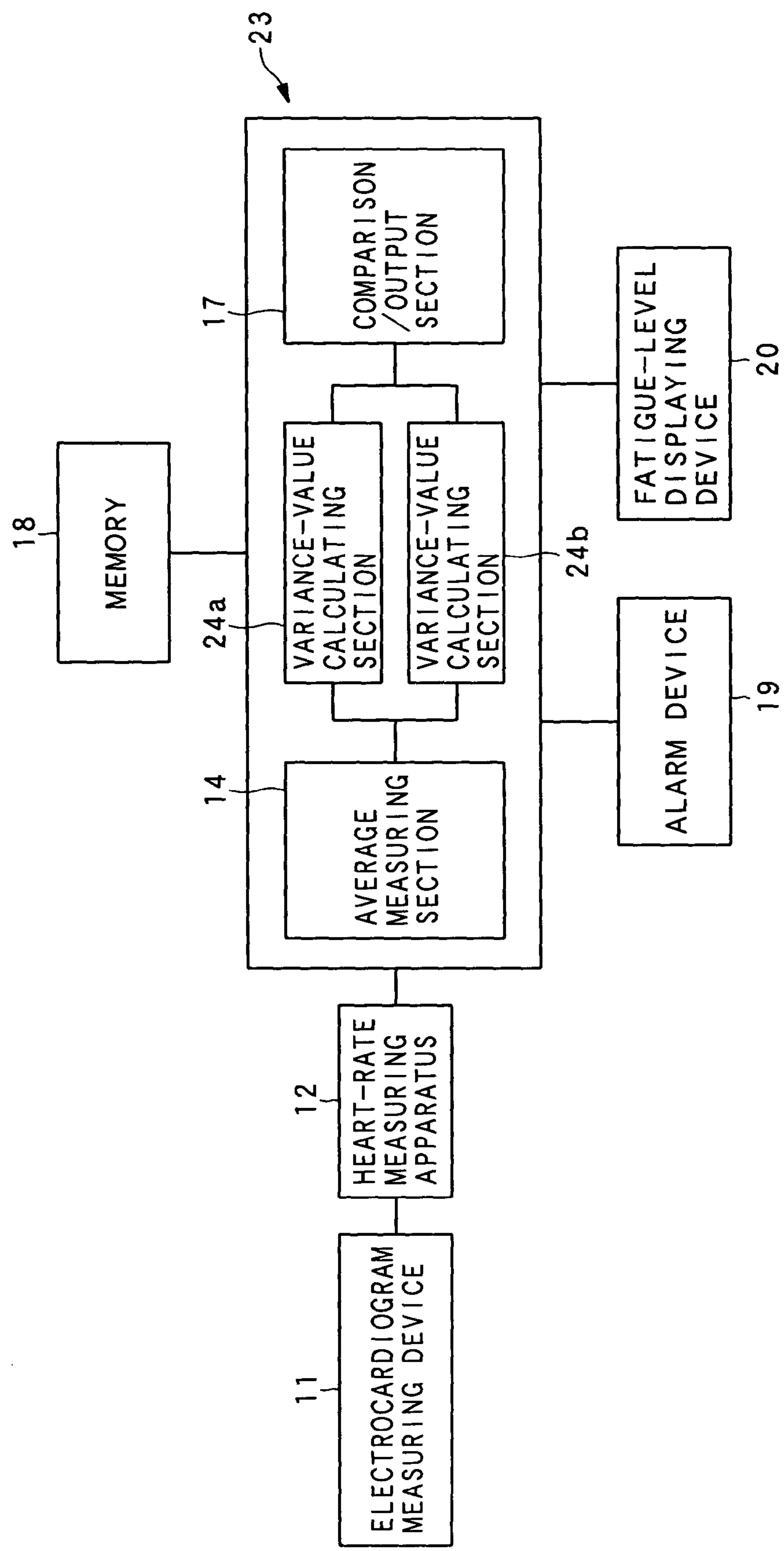
FIG. 7 is a block diagram showing the configuration of a fatigue-level estimation apparatus according to a second embodiment of the present invention.
Figure 8:
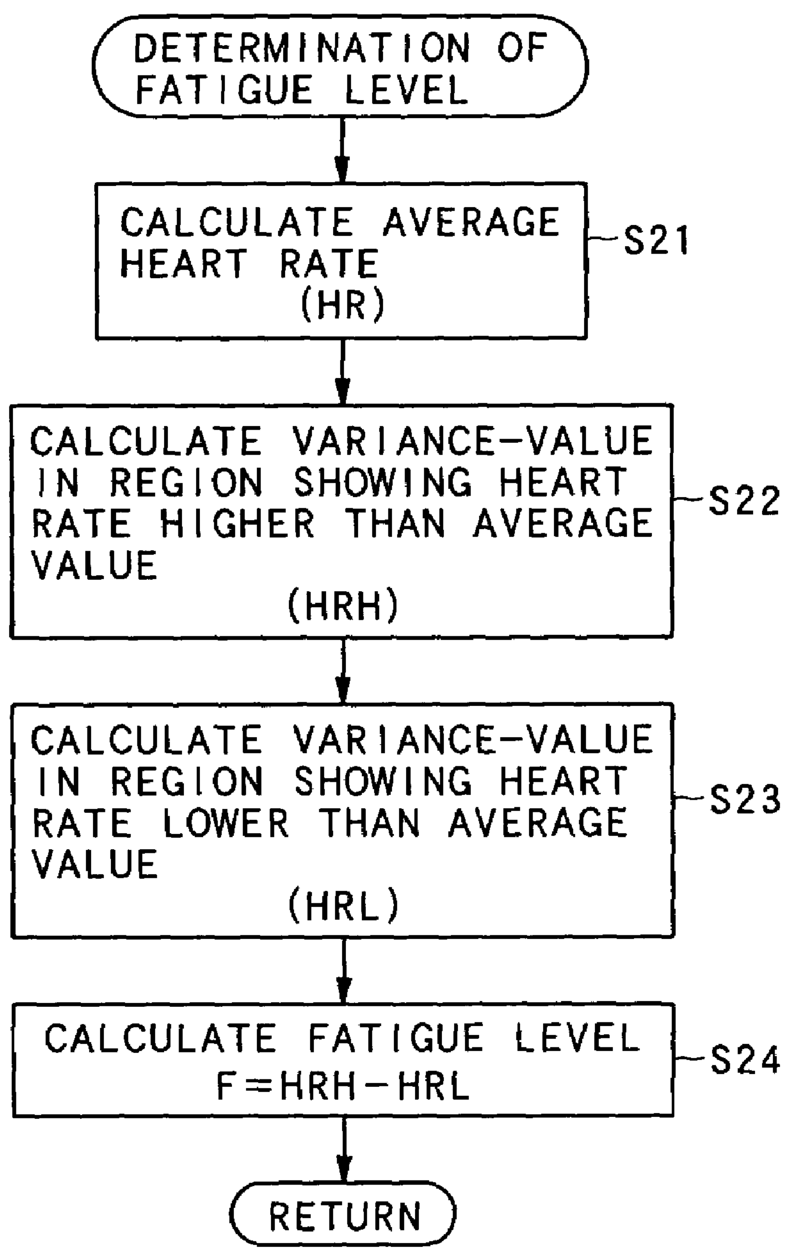
FIG. 8 is a flowchart showing the procedures for fatigue-level estimation processing carried out in the second embodiment.

FIG. 7 is a block diagram showing the configuration of a fatigue-level estimation apparatus according to a second embodiment of the present invention. In FIG. 7, for the sake of a simplified explanation, the identical or similar components to those in the first embodiment are represented by the same references as those in the first embodiment.

As shown in FIG. 7, the fatigue-level estimation apparatus according to the present embodiment comprises an electrocardiogram measuring device 11 detecting electrocardiogram information of an object to estimated; a heart-rate measuring device 12 receiving a heartbeat signal indicative of object's heartbeats from the electrocardiogram information to calculate a heart rate signal changing sequentially in time; and an analysis unit 23 estimating a fatigue level of the object by detecting a sharp and transient rise in the heartbeat in the heart rate signal calculated by the heart-rate measuring device 12. The fatigue-level estimation apparatus further comprises a memory 18 that is in charge of transmitting and receiving data to and from the analysis unit 23 and making the analysis unit 23 work in compliance with a predetermined program for estimation of the fatigue level; an alarm device 19, which is composed of for example, a buzzer, that issues an alarm in cases where the object's fatigue level estimated by the analysis unit 23 exceeds a predetermined value; and a fatigue-level displaying device 20 displaying in real time information about the fatigue level estimated by the analysis unit 23.

The analysis unit 23 according to the present embodiment comprises an average measuring section 14 configured to calculate an average heart rate over a specified period of time on the basis of the heart rate signal; a first variance-value calculating section 24*a* configured to calculate a variance-value in a temporal range during which the heart rate signal is over the average heart rate; a second variance-value calculating section 24*b* configured to calculate a variance-value in a temporal range during which the heart rate signal is below the average heart rate; and a comparison/output section 17 configured to draw a comparison between the variance-values calculated by the first and second variance-value calculating sections 24*a* and 24*b* to output information indicative of a fatigue level.

In this embodiment, of the two variance-value calculating sections 24*a* and 24*b*, one section 24*a* corresponds to the first variance-value calculating unit of the present invention, while the other section 24*b* corresponds to the second variance-value calculating unit of the present invention.

Although the entire fatigue-level estimation processing carried out in the present embodiment complies with the flowchart already shown in FIG. 2, the estimation itself, which is carried out at step S2 in FIG. 2, is different from that described in the first embodiment. That is, the estimation itself is carried out on a flowchart detailed in FIG. 8. This manner is also applied to the embodiments following the second embodiment.

First, the heart-rate measuring device 12 figures out a heart rate every 10 seconds, which is fed to the average measuring section 14 of the analysis unit 13. Hence the average measuring section 14 calculates an average heart rate over a specified measurement period of 100 seconds (i.e., approximately 17 minutes). This average heart rate is denoted as HR (step S21).

Then the variance-value calculating section 24*a* calculates a variance value of the heartbeats in a temporal range during which the heart rates are over the average heart rate HR, the resultant variance value being denoted as "HRH" (step S22).

The remaining variance-value calculating section 24*b* calculates a further variance value of the heartbeats in a temporal range during which the heart rates are blow the average heart rate HR, the resultant variance value being denoted as "HRL" (step S23).

The comparison/output section 17 draws a comparison between the variance-values HRH and HRL calculated by both of the variance-value calculating sections 24*a* and 24*b*, and provides information showing a fatigue level based on compared results (step S24).

Practically, both the variance-values HRH and HRL are subjected to computation for a driver's fatigue level F defined by the following formula:

$$F=HRH-HRL.$$

Figure 9:
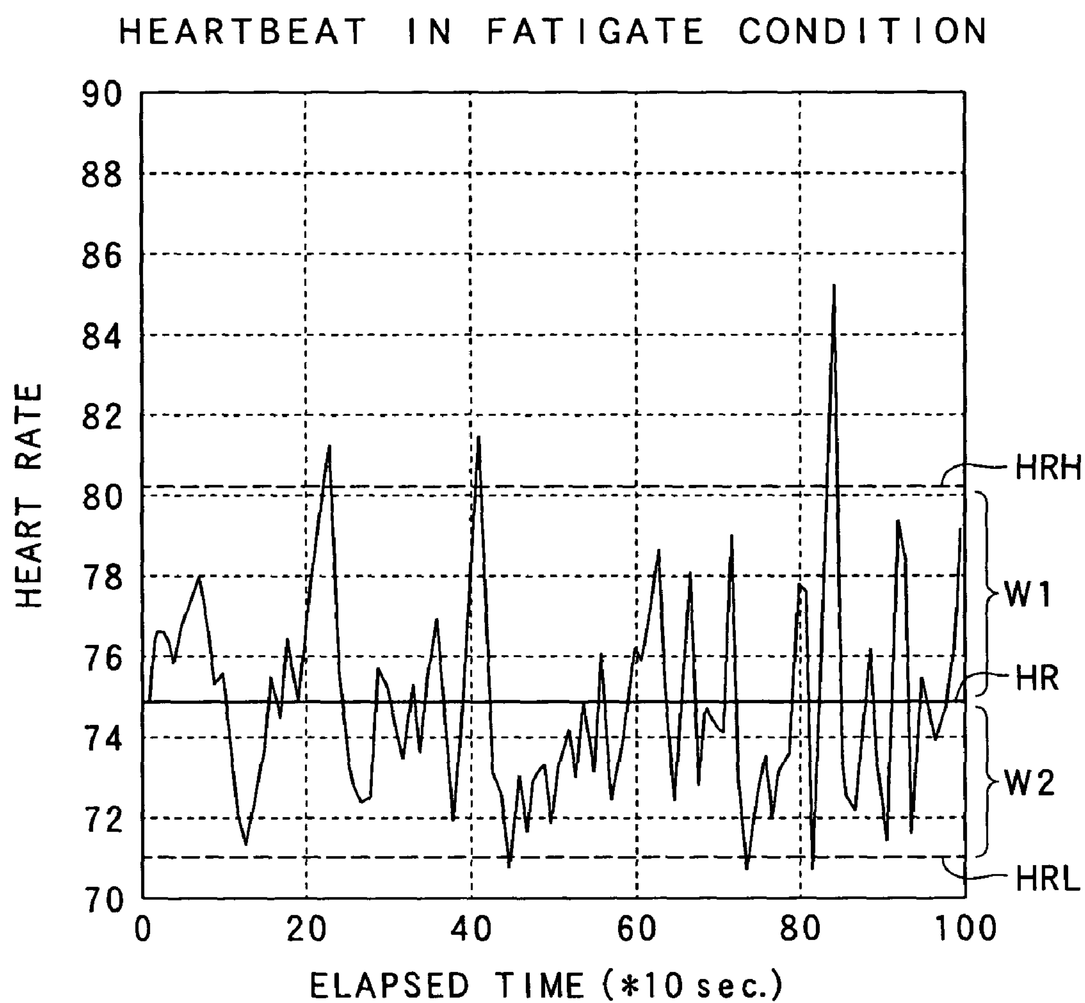
FIG. 9 is a graph indicating temporal changes in the heart rate of a person (object) who is tired.
Figure 10:
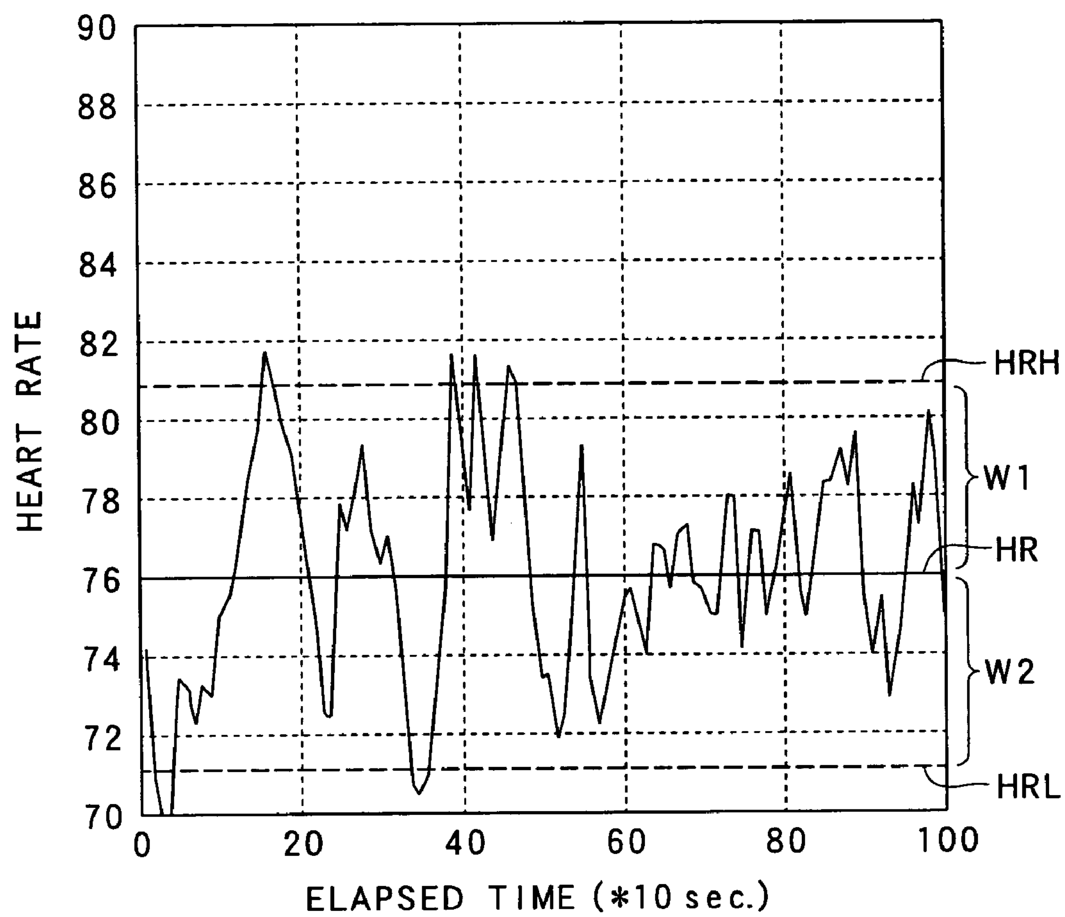
FIG. 10 is a graph indicating temporal changes in the heart rate of a person (object) who is not tired.

Thus, in cases where, as shown in FIG. 9, a relationship of HRH>HRL is established, it is estimated that the fatigue level is high. In contrast, as illustrated in FIG. 10, a relationship of HRH<HRL is established, it is estimated that the fatigue level is low. The value of the fatigue level F is subjected to a real-time display on the fatigue-level displaying device 20 shown in FIG. 6. Incidentally, when the relationship of HRH>HRL is established, an alarm is outputted by the alarm device 19.

In other words, in the present embodiment, within a specified period of time during which variations in the heartbeats continue, a data range W1 of which heart rate is over the average heart rate HR and a further data range W2 of which heart rate is below the average heart rate HR are detected, respectively. These data ranges W1 and W2 then undergo a comparison at the comparison/output section 17. As a result of the comparison, the data range W1 is coarser in data density than the data range W2, as shown in FIG. 9, it is estimated that the fatigue level is high. On the other hand, as shown in FIG. 10, the data range W1 is finer in data density than the data range W2, the estimation that the fatigue level is low is made.

As described above, the analysis unit 23 according to the present embodiment comprises the average measuring section 14 configured to calculate an average heart rate HR over a specified period of time on the basis of the heart rate signal; the first variance-value calculating section 24*a* configured to calculate a variance-value HRH in a temporal range during which the heart rate signal is over the average heart rate HR; the second variance-value calculating section 24*b* configured to calculate a variance-value HRL in a temporal range during which the heart rate signal is below the average heart rate HR; and the comparison/output section 17 configured to draw a comparison between the variance-values HRH and HRL calculated by the first and second variance-value calculating sections 24*a* and 24*b* to output information indicative of a fatigue level. Therefore, without using various types of information in relation to running conditions of a vehicle, the heartbeat information can be used alone to figure out higher-reliability fatigue levels. In the estimation process, the personal differences can be reduced and the erroneous operations can be lessened.

To be specific, within a specified period of time during which variations in the heartbeats continue, a data range W1 of which heart rate is over the average heart rate HR and a further data range W2 of which heart rate is below the average heart rate HR are detected, respectively. These data ranges W1 and W2 then undergo a comparison about their data density at the comparison/output section 17. Thus, the highly reliable estimation on the fatigue level with less influence due to individual differences and less erroneous operation can be achieved using only heartbeat information without using any information on the vehicle.

The other operations and advantages are similar or identical to those in the first embodiment.

Third Embodiment

Figure 11:
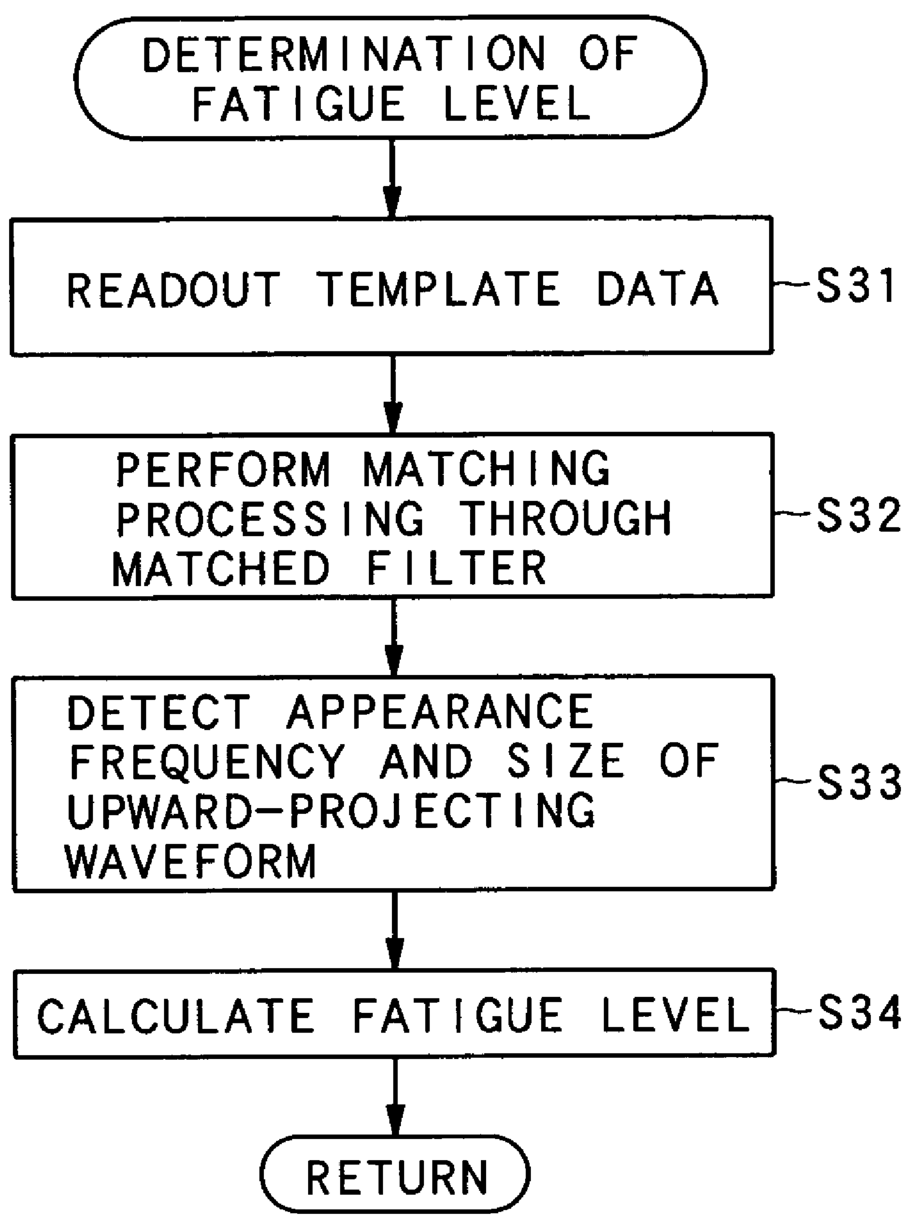
FIG. 11 is a flowchart showing the processing carried out by a fatigue-level estimation apparatus according to a third embodiment of the present invention.

Referring to FIG. 11, a third embodiment of the present invention will now be described.

FIG. 11 is a flowchart showing a third embodiment of the fatigue-level estimation apparatus according to the present invention.

In the present embodiment, template data for estimating a fatigue level is previously stored in the memory 18. Both of the template data and data showing the heart rate signal from the heart-rate measuring device 12 are subjected to matching processing on a matched filter. By making a not-shown detector detect an occurrence frequency and amplitude of an upward waveform resulting from the matching processing, a fatigue level is calculated.

More practically, as explained by the flowchart in FIG. 11, predetermined template data is read out from the memory 18, and then the read-out template data is subjected to the above matching processing with the data of the heart rate signal (steps S31 and S32).

The resultant matching data is then subjected to detection of an occurrence frequency and amplitude of an upward waveform for computation of a fatigue level (steps S33 and S34).

As described above, the fatigue-level estimation in the present embodiment uses the matching processing based on the template data. Thus, like the above embodiments, the estimation of the fatigue level has less influence resulting from individual differences and is far from erroneous operations, while still maintaining high reliability in the estimation.

Fourth Embodiment

Figure 12:
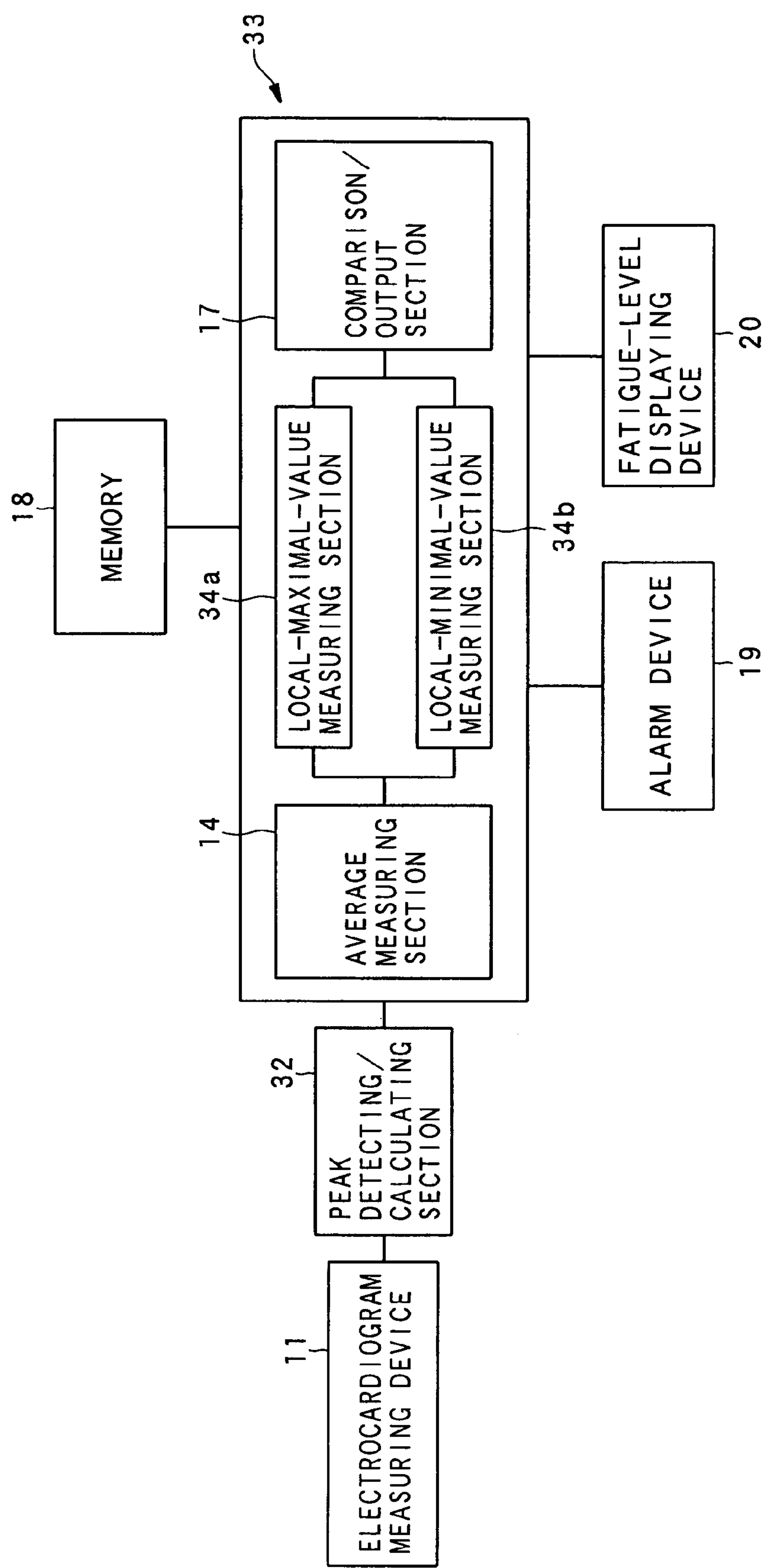
FIG. 12 is a block diagram showing the configuration of a fatigue-level estimation apparatus according to a fourth embodiment of the present invention.
Figure 13A:
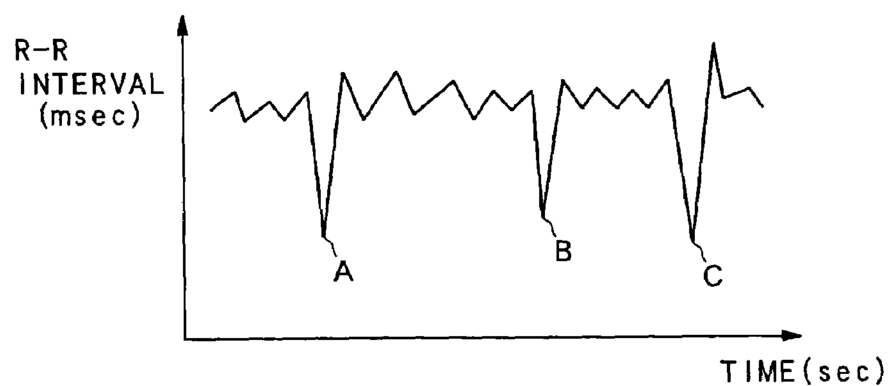
FIGS. 13A and 13B are graphs each showing temporal changes in an R—R interval, which explain a fatigue-level estimation principle according to a fourth embodiment of the present invention.
Figure 13B:
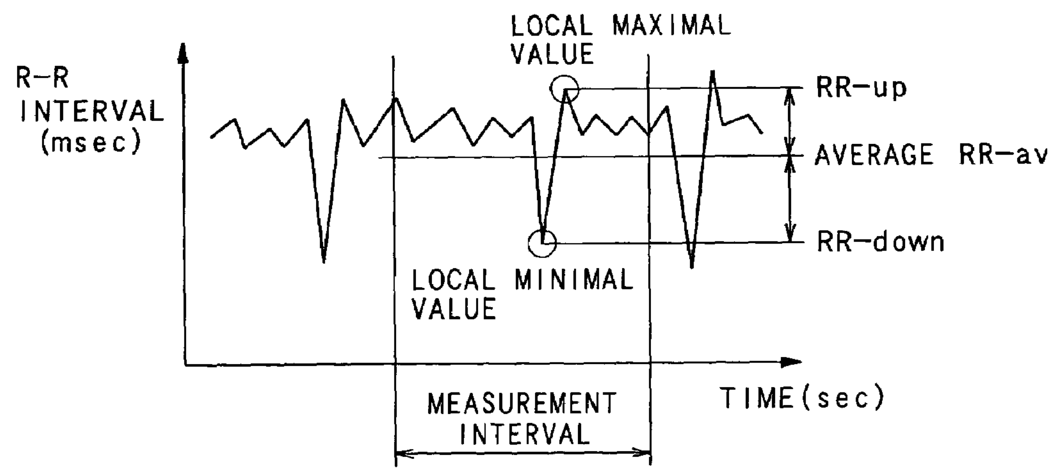
Figure 14:
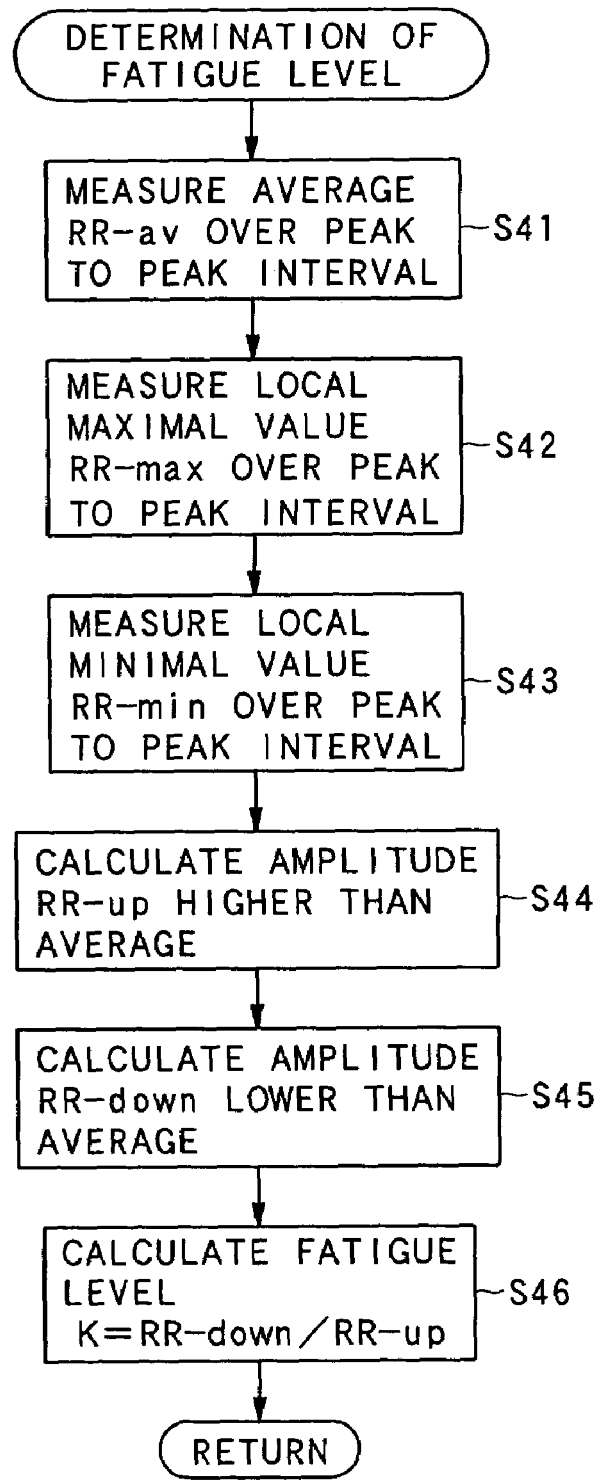
FIG. 14 is a flowchart showing the processing carried out by a fatigue-level estimation apparatus according to a fourth embodiment of the present invention.

Referring to FIGS. 12 to 14, a fourth embodiment of the present invention will now be described.

FIG. 7 is a block diagram showing the configuration of a fatigue-level estimation apparatus according to a fourth embodiment of the present invention.

As shown in FIG. 12, the fatigue-level estimation apparatus according to the present embodiment comprises an electrocardiogram measuring device 11 detecting electrocardiogram information of an object to be estimated; a peak detecting/calculating section 32 configured to detect peak values during a predetermined measurement period of a signal indicative of heartbeats of an object to be estimated and to calculate peak-to-peak intervals (R—R intervals) from the peak values; and an analysis unit 33 configured to measure an average value of the peak-to-peak intervals calculated by the peak detecting/calculating section 32 and to draw a comparison between amplitudes over the average value and a further amplitudes over the average value for estimating a fatigue level of the object.

In the present embodiment, the peak detecting/calculating section 32 corresponds to the peak-to-peak interval calculator of the present invention and the analysis unit 33 composes the fatigue level estimator of the present invention.

The analysis unit 33 is provided with an average measuring section 14 to measure an average of the peak-to-peak intervals calculated by the peak detecting/calculating section 32, a local-maximum-value measuring section 34*a* to measure a local maximum value of the peak-to-peak intervals, a local-minimum-value measuring section 34*b* to measure a local minimum value of the peak-to-peak intervals, and a comparison/output section 17 to draw a comparison between amplitudes over the average of the peak-to-peak intervals and further amplitudes below the average of the peak-to-peak intervals and to output information about a fatigue level.

The principle of fatigue-level estimation processing in this embodiment will now be described in connection with FIGS. 13A and 13B, in which waveforms of R—R intervals are exemplified.

From the electrocardiogram waveform data produced by the electrocardiogram measuring device 11, an R-wave that is a maximum in each cardiac cycle is detected, a reciprocal of an inputted peak-to-peak interval is calculated, and then the reciprocal is multiplied by 60, thus producing a heart rate per minute.

For example, if a driver gets tired during driving a vehicle, the driver's heart rate is lowered, thus R—R intervals becoming larger. It is therefore considered that measurement of downward spiking waveforms A, B and C shown in FIG. 13A will be a good measure for the fatigue levels.

Based on this concept, as illustrated in FIG. 13B, for a specified interval to be measured, an average RR-av of the R—R intervals, a local maximum value RR-max of the R—R intervals, and a local minimum value RR-min of the R—R intervals are measured, respectively. When RR-up, which is a relative amplitude of RR-max to the RR-av level, and RR-down, which is a relative amplitude of RR-min to the RR-av level, are compared to each other within the interval to be measured, the lower amplitudes RR-down becomes larger than the upper ones. A scale K for the fatigue levels is thus introduced as follows:

$$K=PP\text{-down}/PP\text{-up}.$$

Computing this scale K makes it possible to give estimation such that when K>1, the fatigue is large, while when K<1, the fatigue is so large. In this case, $$RR\text{-up}=(RR\text{-max})-(RR\text{-av}) \text{ and}$$

$$RR\text{-down}=(RR\text{-av})-(RR\text{-down}).$$

With reference to FIG. 14, the fatigue-level estimation processing according to the present embodiment will now be described.

First, from electrocardiogram waveform data, the peak detecting/calculating section 32 receives a signal indicative of heartbeats of an object to be estimated, detects peak values existing during a predetermined measurement period, and then calculates peak-to-peak intervals (R—R intervals). The average measuring section 14 then measures an average RR-av from the R—R intervals (step S41).

The local-maximum-value measuring section 34*a* then measures a local maximum value RR-max within the measurement period, whilst the local-minimum-value measuring section 34*b* measures a local minimum value RR-min within the measurement period (steps S42 and S43).

Then, as to the R—R intervals, both of amplitudes RR-up higher than the average RR-av and amplitudes RR-down lower than the average RR-av are calculated, respectively (steps S44 and S45).

The comparison/output section 17 then operates to draw a comparison between the amplitudes RR-up and RR-down so as to provide pieces of information about a fatigue level. In other words, as stated above, the scale K=RR-down/RR-up is calculated and then it is determined whether K>1 or K<1. If a determination of K>1 comes out, the alarm device 19 outputs an alarm, because the fatigue level is high. By contrast, when it is determined that K<1 is, it is considered that the fatigue level is low. In this case, the fatigue level is represented in real time by the fatigue-level displaying device 20 shown in FIG. 6.

As described above, the present embodiment provides the fatigue-level estimation apparatus that uses both types of amplitudes of R—R interval data, which are higher and lower than an average of R—R intervals. Thus, like the above embodiments, the estimation of the fatigue level has less influence resulting from individual differences and is far from erroneous operations, while still maintaining high reliability in the estimation.

In the foregoing various embodiments, though the dedicated apparatuses as described have been used, but this is not a definitive list. As this fatigue-level estimation apparatus, a universal type of computer can be adopted, in which an information recording medium, such as flexible disk or hard disk, is incorporated. On the recording medium, a program for conducting the foregoing fatigue-level estimation processing is stored, so that the computer can read in the program and perform the fatigue-level estimation processing similar or identical to the foregoing embodiments.

In addition, the foregoing embodiments have been described about the application in which the fatigue-level estimation processing is applied to a driver. Alternatively, this fatigue-level estimation processing can be applied to, for example, a person who is in learning. As a result, when the person gets tired beyond a limit, the person will have an alarm to take a rest.

For the sake of completeness, it should be mentioned that the embodiment explained so far is not a definitive list of possible embodiments of the present invention. The expert will appreciate that it is possible to combine the various construction details or to supplement or modify them by measures known from the prior art without departing from the basic inventive principle.

The entire disclosure of Japanese Patent Application No. 2002-250076 filed on Aug. 29, 2002 including the specification, claims, drawings and summary is incorporated herein by reference in its entirety.

What is claimed is:

1. A fatigue-level estimation apparatus comprising:

a heart rate calculator configured to receive a signal indicative of a heartbeat of a person to be estimated to calculate a heart rate signal changing sequentially in time; and a fatigue level estimator configured to estimate a fatigue level of the person by detecting a sharp and transient rise in the heartbeat in the heart rate signal calculated by the heart rate calculator.

2. The fatigue-level estimation apparatus according to claim 1, further comprising an alarm unit configured to issue an alarm when the fatigue level of the person estimated by the fatigue level estimator becomes larger than a predetermined value.

3. The fatigue-level estimation apparatus according to claim 1, further comprising a display unit configured to display pieces of information in relation to the fatigue level of the person estimated by the fatigue level estimator.

4. The fatigue-level estimation apparatus according to claim 1, wherein the fatigue level estimator comprises an average heart-rate calculating unit configured to calculate an average heart rate over a specified period of time on the basis of the heart rate signal;

a first elapsed-time measuring unit configured to measure an elapsed time during which the heart rate signal is over the average heart rate;

a second elapsed-time measuring unit configured to measure an elapsed time during which the heart rate signal is below the average heart rate; and a comparison output unit configured to draw a comparison between the elapsed times measured by the first and second elapsed-time measuring units to output information indicative of the fatigue level.

5. The fatigue-level estimation apparatus according to claim 4, further comprising an alarm unit configured to issue an alarm when the fatigue level of the person estimated by the fatigue level estimator becomes larger than a predetermined value.

6. The fatigue-level estimation apparatus according to claim 4, further comprising a display unit configured to display pieces of information in relation to the fatigue level of the person estimated by the fatigue level estimator.

7. The fatigue-level estimation apparatus according to claim 1, wherein the fatigue level estimator comprises an average heart-rate calculating unit configured to calculate an average heart rate over a specified period of time on the basis of the heart rate signal;

a first variance-value calculating unit configured to calculate a variance-value in a temporal range during which the heart rate signal is over the average heart rate;

a second variance-value calculating unit configured to calculate a variance-value in a temporal range during which the heart rate signal is below the average heart rate; and a comparison output unit configured to draw a comparison between the variance-values calculated by the first and second variance-value calculating units to output information indicative of the fatigue level.

8. The fatigue-level estimation apparatus according to claim 7, further comprising an alarm unit configured to issue an alarm when the fatigue level of the person estimated by the fatigue level estimator becomes larger than a predetermined value.

9. The fatigue-level estimation apparatus according to claim 7, further comprising a display unit configured to display pieces of information in relation to the fatigue level of the person estimated by the fatigue level estimator.

10. A fatigue-level estimation method comprising the steps of:

receiving a signal indicative of a heartbeat of a person to be estimated to calculate a heart rate signal changing sequentially in time; and estimating a fatigue level of the person by detecting a sharp and transient rise in the heartbeat in the calculated heart rate signal.

11. The fatigue-level estimation method according to claim 10, wherein the fatigue level estimating step comprises the sub-steps of:

calculating an average heart rate over a specified period of time on the basis of the heart rate signal;

first measuring an elapsed time during which the heart rate signal is over the average heart rate;

second measuring an elapsed time during which the heart rate signal is below the average heart rate;

drawing a comparison between the measured elapsed times to output information indicative of the fatigue level.

12. The fatigue-level estimation method according to claim 10, wherein the fatigue level estimating step comprises the sub-steps of:

calculating an average heart rate over a specified period of time on the basis of the heart rate signal;

first calculating a variance-value in a temporal range during which the heart rate signal is over the average heart rate;

second calculating a variance-value in a temporal range during which the heart rate signal is below the average heart rate; and drawing a comparison between the calculated variance-values to output information indicative of the fatigue level.

13. The fatigue-level estimation method according to claim 10, further comprising the step of issuing an alarm when the estimated fatigue level of the person becomes larger than a predetermined value.

14. The fatigue-level estimation method according to claim 10, further comprising the step of displaying pieces of information in relation to the estimated fatigue level of the person.

15. A computer-readable program for estimating a fatigue level, the program being executed by a computer provided in a fatigue-level estimation apparatus, the computer achieving the functions of:

heart rate calculating means for receiving a signal indicative of a heartbeat of a person to be estimated to calculate a heart rate signal changing sequentially in time; and fatigue level estimating means for estimating a fatigue level of the person by detecting a sharp and transient rise in the heart rate in the heartbeat signal calculated by the heart rate calculating means.

16. The program according to claim 15, wherein the fatigue level estimating means comprises:

calculating means for calculating an average heart rate over a specified period of time on the basis of the heart rate signal;

first measuring means for measuring an elapsed time during which the heart rate signal is over the average heart rate;

second measuring means for measuring an elapsed time during which the heart rate signal is below the average heart rate;

comparing means for drawing a comparison between the measured elapsed times to output information indicative of the fatigue level.

17. The program according to claim 15, wherein the fatigue level estimating means comprises:

calculating means for calculating an average heart rate over a specified period of time on the basis of the heart rate signal;

first calculating means for calculating a variance-value in a temporal range during which the heart rate signal is over the average heart rate;

second calculating means for calculating a variance-value in a temporal range during which the heart rate signal is below the average heart rate; and comparing means for drawing a comparison between the calculated variance-values to output information indicative of the fatigue level.

* * * * *